US006527702B2

United States Patent
Whalen et al.

(10) Patent No.: US 6,527,702 B2
(45) Date of Patent: Mar. 4, 2003

(54) URINARY FLOW CONTROL DEVICE AND METHOD

(75) Inventors: Mark J. Whalen, Alexandria, MN (US); Lloyd K. Willard, Miltona, MN (US)

(73) Assignee: AbbeyMoor Medical, Inc., Miltona, MN (US)

( * ) Notice: Subject to any disclaimer, the term of this patent is extended or adjusted under 35 U.S.C. 154(b) by 0 days.

(21) Appl. No.: 09/772,088

(22) Filed: Jan. 26, 2001

(65) Prior Publication Data

US 2001/0034470 A1 Oct. 25, 2001

Related U.S. Application Data

(60) Provisional application No. 60/179,038, filed on Feb. 1, 2000.

(51) Int. Cl.[7] .................................................. A61F 2/02
(52) U.S. Cl. ............................ 600/30; 600/29; 600/31; 128/DIG. 25
(58) Field of Search .......................... 600/29, 30, 31, 600/32; 128/DIG. 25

(56) References Cited

U.S. PATENT DOCUMENTS

| | | | |
|---|---|---|---|
| 2,078,686 A | 4/1937 | Rowe | 128/255 |
| 2,450,217 A | 9/1948 | Alcorn | 128/350 |
| 2,687,131 A | 8/1954 | Raiche | 128/349 |
| 3,136,316 A | 6/1964 | Beall | 128/350 |
| 3,495,620 A | 2/1970 | Raimondi et al. | 137/529 |
| 3,630,206 A | 12/1971 | Gingold | 128/349 |
| 3,642,004 A | * 2/1972 | Osthagen et al. | 128/349 R |
| 3,731,670 A | 5/1973 | Loe | 128/1 R |
| 3,812,841 A | * 5/1974 | Isaacson | 128/1 R |
| 3,908,637 A | 9/1975 | Doroshow | 128/2 F |
| 4,217,911 A | 8/1980 | Layton | 128/748 |
| 4,249,536 A | 2/1981 | Vega | 128/349 B |
| 4,301,811 A | 11/1981 | Layton | 128/748 |
| 4,407,301 A | 10/1983 | Steisinger | 128/774 |
| 4,432,757 A | 2/1984 | Davis, Jr. | 604/99 |
| 4,484,585 A | 11/1984 | Baier | 128/748 |
| 4,500,313 A | 2/1985 | Young | 604/280 |
| 4,501,580 A | 2/1985 | Glassman | 604/43 |
| 4,538,621 A | 9/1985 | Jarczyn | 128/748 |

(List continued on next page.)

FOREIGN PATENT DOCUMENTS

WO     WO 00/21462     4/2000     ............. A61F/2/00

OTHER PUBLICATIONS

Vicente, J. et al. *Spiral Urethral Prosthesis as an Alternative to Surgery in High Risk Patients with Benign Prostatic Hyperplasia: Prospective Study.* The Journal of Urology. vol. 142. p. 1504. Copyright 1989.

Fabian, K. M. *Der interprostatische "partielle Katheter".* Urologe. vol. 23. pp. 229–233. 1984.

Fabian, K. M. *Der Intraprostatische "Partielle Katheter".* Urologe. 1980.

*Primary Examiner*—Henry C. Yuen
*Assistant Examiner*—Frederick Nicolas
(74) *Attorney, Agent, or Firm*—Nawrocki, Rooney & Sivertson, P.A.

(57) ABSTRACT

A urinary flow control device having a bladder responsive flow control assembly operatively engaged with an elongate member having proximal and distal ends, and a lumen capable of discharging urine therethrough is provided. The flow control assembly includes first and second fluid containing compartments adapted to be in fluid communication. The flow control assembly is adapted to receive and contain urine from a bladder so as to impinge upon the first fluid containing compartment. The flow control assembly is responsive to increased bladder pressure such that fluid is displaced from the first fluid containing compartment to the second fluid containing compartment to thereby permit select passage of received urine to the lumen of the elongate member for discharge therethrough. A method of controlling urinary flow is likewise provided.

36 Claims, 7 Drawing Sheets

U.S. PATENT DOCUMENTS

| | | | |
|---|---|---|---|
| 4,553,533 A | 11/1985 | Leighton | 128/1 R |
| 4,553,959 A | 11/1985 | Hickey et al. | 604/96 |
| 4,612,939 A | 9/1986 | Robertson | 128/774 |
| 4,721,095 A | 1/1988 | Rey et al. | 128/1 R |
| 4,737,147 A | 4/1988 | Ferrando et al. | 604/96 |
| 4,781,677 A | 11/1988 | Wilcox | 604/28 |
| 4,792,335 A | 12/1988 | Goosen et al. | 604/323 |
| 4,865,030 A | 9/1989 | Polyak | 128/321 |
| 4,865,588 A | 9/1989 | Flinchbaugh | 604/129 |
| 4,873,990 A | 10/1989 | Holmes et al. | 128/748 |
| 4,909,785 A | 3/1990 | Burton et al. | 604/54 |
| 4,932,938 A | 6/1990 | Goldberg et al. | 604/96 |
| 4,934,999 A | 6/1990 | Bader | 600/29 |
| 4,946,449 A | 8/1990 | Davis, Jr. | 604/256 |
| 5,030,199 A * | 7/1991 | Barwick et al. | 600/29 |
| 5,041,092 A | 8/1991 | Barwick | 604/104 |
| 5,059,169 A | 10/1991 | Zilber | 604/8 |
| 5,088,980 A | 2/1992 | Leighton | 600/30 |
| 5,090,424 A | 2/1992 | Simon et al. | 128/885 |
| 5,112,306 A | 5/1992 | Burton et al. | 604/101 |
| 5,114,398 A | 5/1992 | Trick et al. | 600/29 |
| 5,140,999 A * | 8/1992 | Ardito | 128/885 |
| 5,234,409 A | 8/1993 | Goldberg et al. | 604/96 |
| 5,250,029 A | 10/1993 | Lin et al. | 604/96 |
| 5,271,735 A | 12/1993 | Greenfeld et al. | 604/266 |
| 5,360,402 A | 11/1994 | Conway et al. | 604/97 |
| 5,366,506 A | 11/1994 | Davis | 623/12 |
| 5,380,268 A | 1/1995 | Wheeler | 600/30 |
| 5,385,563 A | 1/1995 | Gross | 604/284 |
| 5,427,115 A | 6/1995 | Rowland et al. | 128/756 |
| 5,429,620 A | 7/1995 | Davis | 604/283 |
| 5,437,604 A | 8/1995 | Kulisz et al. | 600/30 |
| 5,483,976 A * | 1/1996 | McLaughlin et al. | 128/885 |
| 5,512,032 A | 4/1996 | Kulisz et al. | 600/29 |
| 5,527,336 A | 6/1996 | Rosenbluth et al. | 606/192 |
| 5,711,314 A * | 1/1998 | Ardito | 128/885 |
| 5,713,877 A * | 2/1998 | Davis | 604/246 |
| 5,718,686 A | 2/1998 | Davis | 604/101 |
| 5,724,994 A * | 3/1998 | Simon et al. | 128/885 |
| 5,735,831 A | 4/1998 | Johnson et al. | 604/280 |
| 5,752,525 A * | 5/1998 | Simon et al. | 128/885 |
| 5,762,599 A * | 6/1998 | Sohn | 600/30 |
| 5,766,209 A | 6/1998 | Devonec | 604/8 |
| 5,776,081 A | 7/1998 | Kreder | 600/593 |
| 5,785,641 A | 7/1998 | Davis | 600/30 |
| 5,813,974 A * | 9/1998 | Guardia | 600/29 |
| 5,864,961 A | 2/1999 | Vaughan | 33/512 |
| 5,876,417 A | 3/1999 | Devonec et al. | 606/192 |
| 5,916,195 A | 6/1999 | Eshel et al. | 604/96 |
| 5,964,732 A | 10/1999 | Willard | 604/117 |
| 5,971,967 A | 10/1999 | Willard | 604/264 |
| 5,976,068 A * | 11/1999 | Hakky et al. | 600/29 |
| 6,022,312 A * | 2/2000 | Haussy et al. | 600/29 |
| 6,033,413 A * | 3/2000 | Mikus et al. | 606/108 |
| 6,056,699 A | 5/2000 | Sohn et al. | 600/561 |
| 6,083,179 A | 7/2000 | Oredsson | 600/587 |
| 6,105,580 A * | 8/2000 | Von Iderstein et al. | 128/885 |
| 6,132,365 A * | 10/2000 | Sigurdsson | 600/29 |
| 6,167,886 B1 * | 1/2001 | Engel et al. | 128/885 |
| 6,221,060 B1 * | 4/2001 | Willard | 604/264 |
| 6,234,956 B1 * | 5/2001 | He et al. | 600/30 |

\* cited by examiner

URINARY FLOW CONTROL DEVICE AND METHOD

This is a regular application filed under 35 U.S.C. §111(a) claiming priority under 35 U.S.C. §119(e) (1), of provisional application Serial No. 60/179,038, having a filing date of Feb. 1, 2000, filed under 35 U.S.C. §111(b).

TECHNICAL FIELD

The present invention generally relates to medical devices, and more particularly to bladder control devices, and still more particularly to an indwelling urinary flow control device for the treatment of urinary incontinence.

BACKGROUND OF THE INVENTION

Although a variety of treatment devices and/or methodologies have been developed, urinary incontinence for both men and women remains a persistent problem. Heretofore known approaches to the problem are generally recognized as either remedial or corrective. Remedial approaches (i.e., those primarily dealing with the effects of incontinence) have primarily included the use of catheters in combination with collection bags or the like. As circumstances warrant, the wearing of special fluid retaining pants has been an option, all be it an undesirable one, for both social and practical reasons.

Remedial approaches are almost always less attractive than corrective approaches, which generally require the placement or implantation of an indwelling device within the urethra. In general terms, it is the goal of such devices to provide a valving system for a patient's bladder, which system is placed directly in the urethra, and adjacent the bladder. The valving system is ideally activated by the patient upon sensing an urge to urinate, such urge being generally generated at about 20 centimeters of water pressure (20 cm $H_2O$), and deactivated when the bladder has been sufficiently emptied.

Some of the problems and disadvantages of known devices include the deleterious effects (i.e., pitting, depositions, etc.) associated with the urethral environment upon critical device components (e.g., valve actuators, flow conduits, etc.) which at a minimum render such devices less effective, and which at a maximum, cause device component failure or render the device wholly ineffective, which necessitates emergent removal and, as the case may be, urinary tract damage repair. Problems of device leakage, or less than complete emptying of the bladder are also widely known. Furthermore, issues surrounding device deployment and fit, positioning, repositioning, and retention (i.e., sufficient anchoring) have also been well documented.

Device features are primarily dictated by the anatomical and physiological environment into which they are to be placed. In light of know devices and methodologies, it has become better appreciated that there are several essential requirements which must be met for an indwelling urinary flow control device so as to be effective.

First, the flow control device must not completely occlude urethral passage when intra-bladder pressures are excessive for an extended period of time. It is a widely held view among clinical urologists that on occasions when the bladder is pressurized to beyond approximately 40 cm $H_2O$ for more than about 2 hours, an individual is in danger of permanent injury to the kidneys. For this reason, it is desirable for a flow control device to allow passage of at least as much urine, volumetrically, as is being produced by the kidneys once the bladder pressure has reached a threshold value (i.e., approximately 40 cm $H_2O$).

Second, physical straining due to lifting, laughing, coughing, and other "exertions" may produce inter-abdominal forces on the bladder, which may translate to pressures in excess of 40 cm $H_2O$ for a short time interval or duration. Such inadvertent stresses must not cause appreciable leakage, even though they may momentarily exceed approximately 40 cm $H_2O$ for short durations. Such pressure surges are a natural event, which may be frequently encountered.

Third, the flow control device must allow for remote or natural initiation without physically touching or otherwise contacting the flow control device in order to provide the most protection against introduction of bacteria, which would be likely to contribute to urinary tract infections (UTIs). It is further advantageous that the initiation be painless, sterile, non-invasive, repeatable, not dependent upon hardware that is expensive, cumbersome, difficult to operate or objectionable.

Fourth, the flow control device must be stable with respect to position (i.e., a physiologically properly deployed and stable position), and comfortable to wear, as the urinary tract is sensitive to contact. Inter-urethral stents have been utilized within the male urethra within the prostatic region with many users foregoing such devices for alternate therapies due to feelings of discomfort and/or pain. Many flow control devices have similarly been evaluated for urinary incontinence for females. Based upon clinical findings, many have been shown to be uncomfortable, thus severely retarding their utility as a therapy. Other devices have migrated into the bladder, or have been expelled under straining conditions.

Fifth, flow control devices must have longevity of operation. Working components that are exposed to urine are susceptible to encrustation, which may compromise device operation and thereby place a wearer at risk of injury or even death. Intraurethral flow control devices must not quickly lose functional operation due to either mechanical failure, or blockage of flow passages. This is exceedingly important for a male due to the more difficult, and more inconvenient, removal associated with typical flow control devices.

SUMMARY OF THE INVENTION

A urinary flow control device having a bladder responsive flow control assembly operatively engaged with an elongate member having proximal and distal ends, and a lumen capable of discharging urine therethrough is provided. The flow control assembly includes first and second fluid containing compartments adapted to be in fluid communication. The flow control assembly is adapted to receive and contain urine from a bladder so as to impinge upon the first fluid containing compartment. The flow control assembly is responsive to increased bladder pressure such that fluid is displaced from the first fluid containing compartment to the second fluid containing compartment to thereby permit select passage of received urine to the lumen of the elongate member for discharge therethrough. A method of controlling urinary flow is likewise provided.

Alternate embodiments of the device are primarily directed to alternate encasements thereof. More particularly, the exterior surface of the devices are adapted for ease of placement, namely secured placement via an anchoring mechanism. It is especially advantageous that the anchoring mechanism be responsive to variations in anatomy. Although this may be the case, a common operational premises underlays each.

The device and method of the subject invention provides for flow initiation subject to the flow related criteria previously detailed by providing, among other things, functions that are two fold and parallel. First, the subject device provides a unique design and function in which the critical switching elements of the flow control assembly, namely the mechanisms associated with the first and second fluid containing components, are sealed from the urine. Functionally, flow initiation is accomplished by magnetically opening a passageway within a sealed system which allows the "unlatching" of the device by the release of a fluid locked or blocked condition within a first closed system (i.e., first fluid containing compartment).

Unlatching occurs when an external switch actuator (e.g., a magnet) is introduced exterior but proximal to the body (e.g., in the case of magnetic actuating means, to the anterior region of the body near the pubic bone). Urine flow then begins as the first fluid containing compartment is allowed to deform (i.e., partially collapse) due to fluid being hydraulically shuttled from the first fluid compartment to an adjacent reservoir (i.e., from the first to second fluid containing compartments). This dynamic device configuration permits urine to pass from the bladder and to the urethra for discharge, with the "work" required to deflect the first fluid containing compartment and transport fluid from the first to second compartment provided by the internal pressure within the bladder.

When the external magnet is removed, the device will not prohibit discharge of urine from the bladder to the urethra during urination, or immediately post urination, but only when the external magnet is again brought into communication with the device. This assures complete emptying of the bladder without requiring continual straining, even when the natural micturation episode of the bladder is concluded. In the event that a user's bladder will not produce sufficient pressure to empty his or her bladder, use of the subject device permits a more complete drainage of the bladder of urine. When urination or voiding is complete, the user simply brings in the external magnet to "unlatch" the device a second time. After a brief period the device will be reset into its static configuration. This occurs due to the pressure responsiveness of the flow control assembly, particularly the fact that the first fluid containing member is dynamically responsive to bladder pressure (i.e., will return to a pre-collapsed, reset condition). With the external magnet removed, the device is thereby reset (i.e., placed in a static configuration) so as to withstand the filling pressure within the bladder.

The subject invention allows for the isolation of the critical functional components from the severe corrosive environment encountered within the bladder and urethra. The magnetic latching function of this device does not provide the work to move fluid, but rather enables or disables the movement which must occur internal to the fluid control assembly to permit controlled, or at least regulated, passage of urine from the bladder into the urethra.

A further desirable feature of the embodiments of the subject invention is the relief of over pressurization within the bladder, while simultaneously protecting the patient from involuntary openings when pressure surges occur due to laughing, or sneezing. This control is provided by selectively allowing the limited displacement of the fluid control assembly components at discrete predetermined pressures or pressure ranges.

The material characteristics and geometry of the first fluid containing compartment specifically determine the initiation pressure for over-pressure or venting flow. When sufficient fluid is transported between the fluid containing compartments, a relative collapse of the first fluid containing compartment will manifest, and a controlled passage (i.e., leakage) of urine from the bladder to the urethra will occur. The extent of leakage is regulated by the volume of fluid that is transferred (i.e., displaced) into the second fluid containing compartment as a function of time in an over-pressure event. Upon relief of excess pressure, the first fluid containing compartment tends towards its static configuration so as to cause vacuum motivated retrieval of the fluid from the second fluid containing compartment into the first fluid containing compartment, thereby returning the device to a static configuration representative of an equilibrium condition or status.

The device of the subject invention may be configured with features of co-pending applications Ser. No. 09/411,491, "Device with Anchoring System"; Ser. No. 09/340,491, "Apparatus with Position Indicator and Methods of Use Thereof" which is a continuation of U.S. Pat. No. 5,964,732; and, No. 60/168,306, "Magnetic Retrieval Device and Method of Use", the entire disclosures of which are incorporated herein by reference.

The foregoing and other objects, features, and advantages of the invention will be apparent with reference to the figures and from the following DETAILED DESCRIPTION OF THE INVENTION. The figures are not necessarily to dimensional or geometric scale, nor do they necessarily represent structures in accurate or representative relative scale. Emphasis rather is placed upon illustrating principals of the invention in a clear manner.

DETAILED DESCRIPTION OF THE INVENTION

Figure 1:
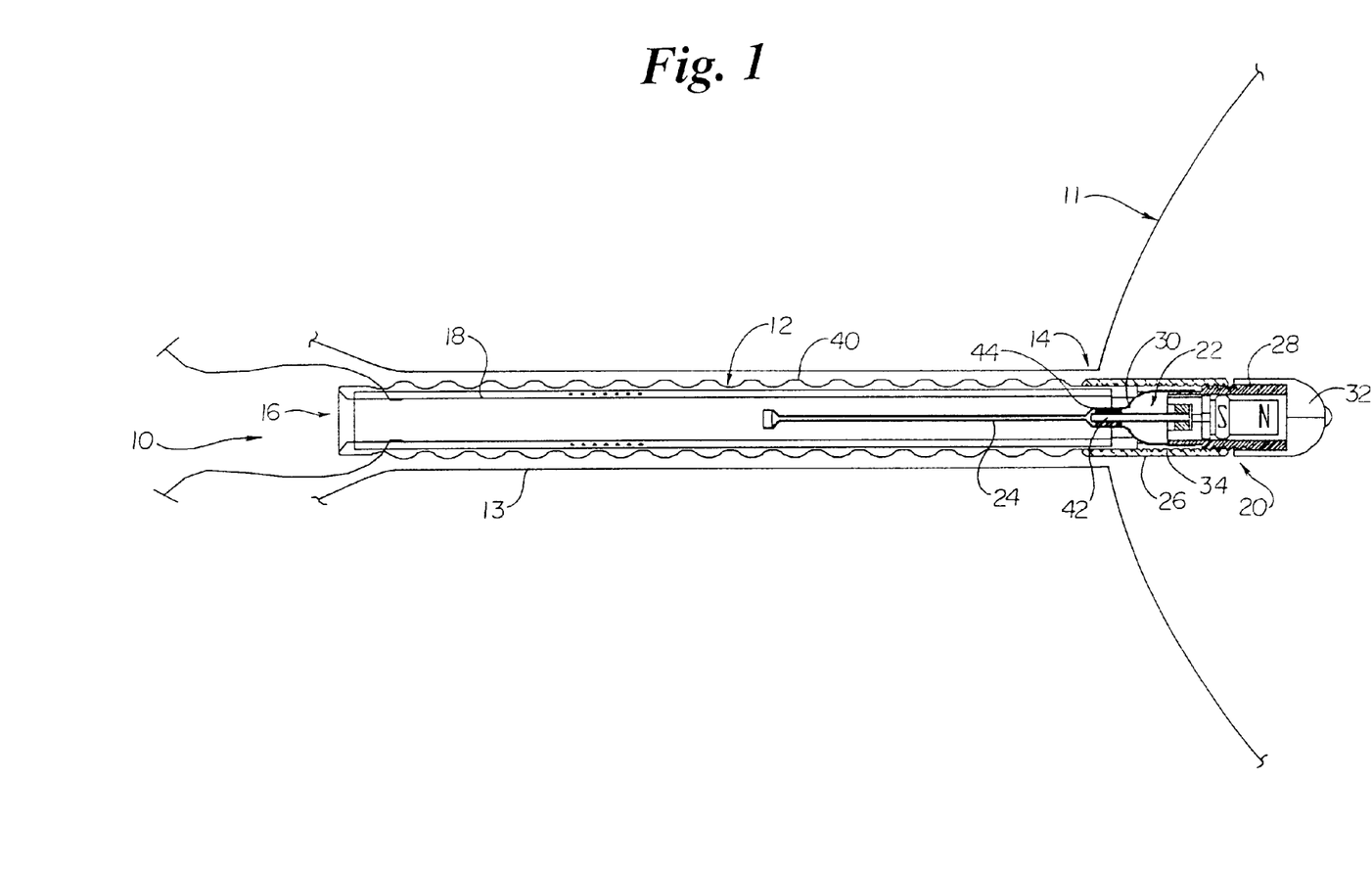
FIG. 1 is a longitudinal sectional view of the flow control device of the subject invention illustrating a static condition for the device while in situ, namely within a male urinary system.
Figure 2:
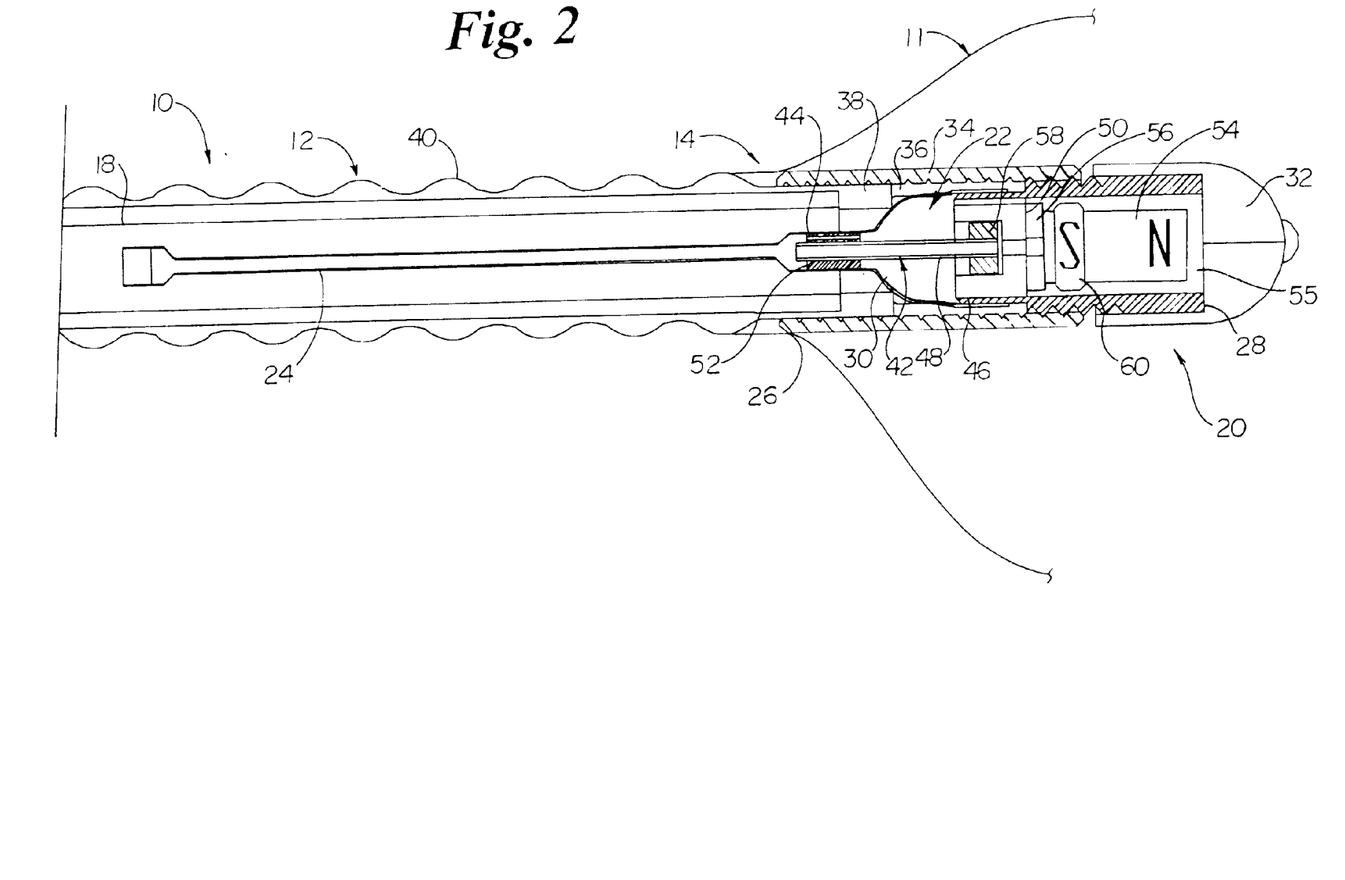
FIG. 2 is an enlarged view of the proximal end of the device of FIG. 1, particularly illustrating the structures associated therewith, and relationships therebetween.

Generally referencing the figures, more particularly to FIGS. 1 and 2, there is shown a urinary flow control device 10 which generally includes an elongate member 12 having proximal 14 and distal 16 ends and a lumen 18 capable of discharging urine therethrough, and a flow control assembly 20, operatively joined to the elongate member 12, having first 22 and second 24 fluid containing compartments adapted to be in fluid communication with each other. The flow control assembly 20, which is generally adapted to receive and contain urine from the bladder so as to impinge upon the first fluid containing compartment 22, is designed to be responsive to increased bladder pressure such that fluid is displaced from the first fluid containing compartment 22 to the second fluid containing compartment 24. Such responsiveness permits the select passage of urine from the bladder to the lumen 18 of the elongate member 12 for discharge into and through the urethra.

The urinary flow control device of the subject invention is secured in the male with an end (i.e., the "proximal" end) of the device positioned such that it is within the portion of the urethra that is commonly referred to as the bladder neck. So positioned, the device extends past the urethral sphincter(s) with its distal end terminating in the bulbous urethra. In the female anatomy, the proximal end of the device is also preferably positioned such that it is within the bladder neck. The device is positioned such that the distal end terminates exterior the meatus. While the encasements of the male and female devices may differ (e.g., see FIGS. 5 and 5A, and FIG. 6), common operational premises, and structures, underlay each.

The urinary flow control device 10 generally has static (e.g., FIGS. 1 and 2) and dynamic (e.g., FIGS. 3, 4, and 4A) configurations which correspond to urine "blocking" and urine "draining" conditions, each condition, and thereby device configuration, being responsive to physiologic conditions of the bladder. As will later be explained in further detail, and will become apparent with a further discussion of the preferred embodiments, in a static configuration for the device, the flow control assembly 20 blocks urine from entering the lumen 18 of the elongate member 12, while in a dynamic configuration, whether it be initiated voluntarily (i.e., intentional as by manual manipulation of the device) or non-voluntarily (i.e., by discrete pressure impulse transmitted by the bladder, as by coughing, laughter, etc.), the flow control assembly 20 permits regulated urine drainage from the bladder to the urethra.

Having provided an overview of the device, more particularly the configurations and functions associated therewith, attention is again directed to FIGS. 1 and 2 wherein there is shown the device 10 of the subject invention indwelling with respect to a male bladder 11. The device 10, as illustrated, shows a static configuration (i.e., closed or urine blocking position), namely the internal components thereof cooperatively arranged and engaged so as to prohibit urine from passing from the bladder 11 to the urethra 13.

The flow control assembly 20, which includes first 22 and second 24 fluid containing compartments, is operatively joined to the elongated member 12. Such operative connection may be made directly, as by the direct union of the flow control assembly 20 to the elongate member 12 (e.g., by joining select elements of the flow control assembly 20, for instance the first fluid containing compartment 22, or structures associated therewith, to the elongate member 12), or indirectly joining the assembly 20 to the elongate member 12 as by a casing 26, or the like, as is illustrated and will be further detailed.

The first fluid containing compartment 22, or capsule, is substantially defined by a minimally rigid component 28 from which a resilient dome-like membrane 30 extends. The casing 26, which appears as a cylinder or sleeve, is generally shown directly joining a portion of the elongate member 12 (i.e., exterior proximal end) to a portion of the flow control assembly 20, more particularly, the minimally rigid member 28 of the first fluid containing compartment 22). A cap 32, which is generally attached to the flow control assembly 20 (i.e., to the rigid base 28 of the first fluid containing compartment 22), defines a proximal end for the device 10, and more particularly as shown, delimits the proximal extent of the first fluid containing compartment 22. The cap 32 may alternately and suitable be joined to, or be integral with the casing 26, or may otherwise be suitably arranged or even omitted as the case may be (e.g., where the rigid component 28 has a closed end, as opposed to a sleeve-like configuration as shown in the figures).

The casing 26 is generally adapted to receive urine from the bladder, as for instance by a series of radially spaced portals 34, such that the first fluid containing compartment 22, vis-a-vis the membrane 30, may be responsive to bladder pressure. In-flowing urine will generally occupy a void space 36 bounded by a sealing element 38 (i.e., ring), the casing 34, and the flow control assembly 20 (i.e., first fluid containing compartment 22) for containment therein.

The sealing element 38 is disposed so as to seal the proximal end of the lumen 18 from the flow control assembly 20, more particularly, the resilient membrane 30 of the first fluid containing compartment 22 sealingly engages the sealing element 38 to prohibit entry of urine into the lumen 18. The sealing element 38 may be integral to the exterior surface or skin 40 of the elongate member 12, as shown, or a discrete structure positioned with respect to the proximal end of the elongate member 12 and the casing 26 so as abut the dome-like element 30.

The dome 30 is of a specific geometry (e.g., semihemispherical) and material (e.g., low durometer silicone), the two properties being interrelated (i.e., jointly defining the performance character of the dome or membrane), so as to reversibly deform under specific pressure conditions (i.e., be pressure responsive), and thereby prohibit or permit, as the case may be, passage of urine from the bladder to the urethra. The material from which the dome is constructed preferably has an inherent memory. This is evident functionally as the dome initially collapses at high pressure and subsequently restores to its original shape at a lower pressure. This attribute, in combination with the latching sequence, enables the device to be maintained in an, dynamic configuration until urine within bladder has returned to a relative low or no pressure state.

The fluid containing compartments 22, 24 are linked by primary 42 and secondary 44 fluid passages or paths. The primary fluid passage 42 is capable of selective passage of fluid between the fluid compartments in furtherance of passing urine from the bladder to the urethra. A conduit body 46 generally traverses the first fluid containing compartment 22 and supports a conduit 48 which extends distally (i.e., toward the elongate member 12) from a proximal surface 50 thereof. The conduit 48 is distally supported or positioned with respect to the membrane 30 by a collar-like element 52 which surrounds the conduit 48 and effectively defines an interface for the fluid containing compartments. The distal end of the conduit 48 is shown within the second fluid containing compartment 24.

A latch mechanism 54, in the form of a magnet, is positioned to prevent or prohibit inadvertent access of fluid from the first fluid compartment 22 to the second fluid compartment 24 via the primary passage 42. The latch 54 generally occupies the cavity 55 defined by the conduit body 46, rigid first fluid containing member 28, and the end cap 32. The magnet 54 is maintained in a "latched" condition against the proximal opening of the primary fluid passage 42 to prohibit fluid flow between the fluid compartments, preferably indirectly via a further sealing element or sealing surface 56, by a second magnetic surface 58 contained within the conduit housing 46.

The latch 54 (i.e., magnet) has a centering collar 60 located about the outer perimeter thereof to properly align it with the primary fluid passage 42 for sealing engagement therewith. The magnet 54 is preferably comprised of a high flux density magnetic Neodymium 27 material. The small size of the magnet provides for a very long actuation distance with only a small external magnet. Magnet 54 is cylindrical in shape, preferable dimensioned to be about 0.125 inches in diameter by about 0.250 inches long, however, the actuation distance is dependent on the external magnet size and magnetic flux density, with actuation distances in excess of 9 centimeters easily accomplished with a small external activation magnet 62. Magnet 54 is preferably coated with epoxy, paraxylene, or other substance known to eliminate or at least reduce the production of magnetic particulate, and thereby the known problems associated therewith.

The secondary fluid passage 44 extends through the collar-like element 52 which, as previously noted, generally positions the conduit 48 of the primary fluid passage 42 relative to the membrane 30, and otherwise separates the first fluid compartment 22 from the second fluid compartment 24. The secondary passage 44, which allows fluid communication between the fluid containing compartments, is utilized in an over-pressure protection sequence (i.e., provides automatic pressure relief to the bladder by displacement of fluid from the first fluid containing compartment 22 to the second fluid containing compartment 24). The important consideration with respect to the over-pressure protection mechanism is that the secondary fluid containing compartment 24 be in fluid communication with the first fluid containing compartment 22 at all times so as to received displaced fluid therefrom, as during instances of increased or increasing bladder pressure, most notably those approaching or exceeding about 20 cm $H_2O$ for brief periods.

The second fluid containing compartment 24 is shown longitudinally extending within the lumen 18 of the elongate member 12, though it need not be so positioned. Device size, performance, and manufacturing costs, to a great extent, determine the specific nature as well as the positioning of the second fluid containing compartment. The second fluid containing compartment 24, which in effect functions as a reservoir for the first fluid containing compartment 22, is preferably expansible or deformable, however, a more rigid or even fixed walled compartment may be suitable, and is within the scope of the present invention.

Figure 3:
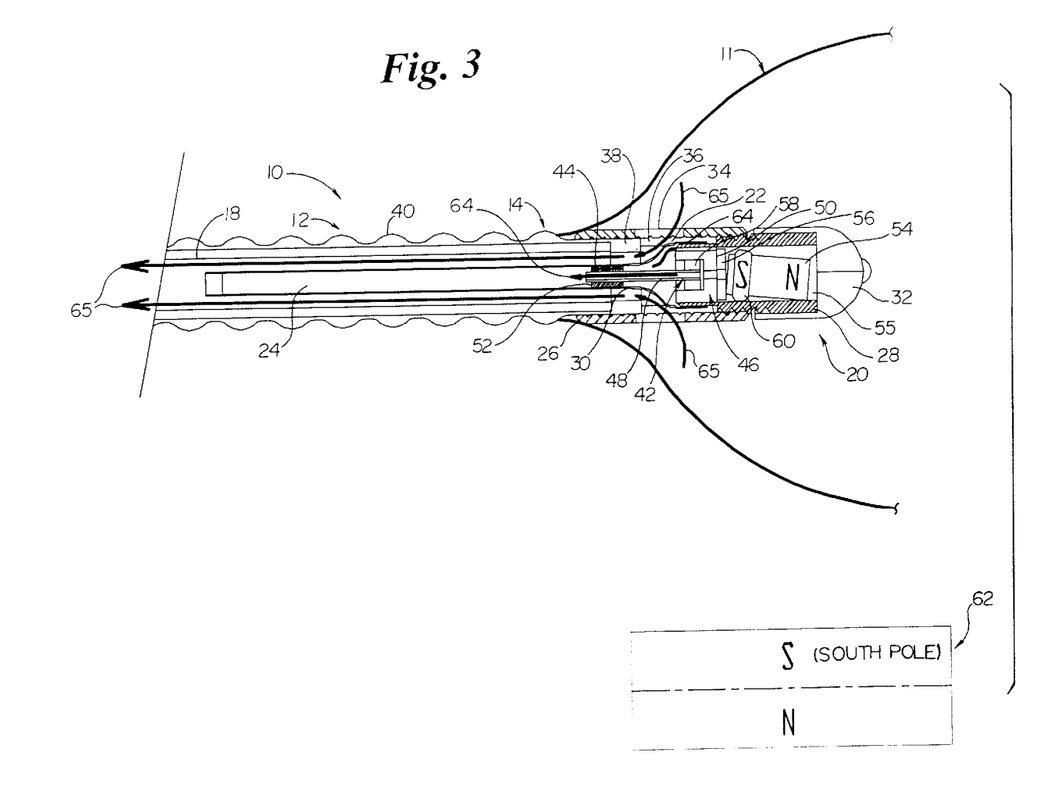
FIG. 3 is an enlarged view of the proximal end of the device of the subject invention, similar to that of FIG. 2 but instead showing a dynamic condition for the device, with urine freely entering the lumen of the elongate member.

Referring now to FIG. 3, the urinary flow control device 10 is shown in a dynamic state, namely an externally initiated state. External or voluntary initiation occurs when external magnet 62 is held approximately perpendicular to the at rest orientation of magnet 54. Magnet 54 is illustrated displaced slightly within cavity 55. This displacement occurs because the poles of the magnet 54 are either attracted to, or repelled away from the approaching poles of the external magnet 62. The initiated state occurring due to the north pole of magnet 54 is illustrated attracted to the south pole of magnet 62, however, pole orientation is not critical. The initiation mechanism functions nearly identically, whether by opposite poles attracting, or like poles repelling. Subsequent to the "tipping" of magnet 54, fluid is in communication with the second fluid containing compartment 24 by the pathway illustrated by arrows 64 as a result of the primary fluid passage 42 being accessible to fluid by separation of the sealed interface between the distal extremity of magnet 54 and conduit body 46. Fluid will not be transferred along the passageway shown by arrows 64 until there is sufficient pressure within the bladder for urine to displace (i.e., collapse) the membrane 30 of the first fluid containing compartment 22, thereby reversibly deflecting it away from ring seal 38. Membrane 30, in a static device configuration, blocks or seals passage into lumen 18, whereas in a dynamic configuration for device 10, membrane 30 permits passage into lumen 18, in effect performing as a switching element.

Prior to a sufficient volume of fluid being transferred into reservoir 24, the deformable dome 30 remains in sealed contact with ring seal 38. The passage of urine from the bladder to the elongate member 12 of urethral flow apparatus 10 only occurs when the deformable dome 30 has been forced away from sealing ring 38. The magnetic initiation sequence opens or restricts the fluid pathway illustrated by arrows 64 when the magnet 62 is respectively introduced and removed from the region external the body which is roughly perpendicular of the urethral flow apparatus 10. Second fluid containing compartment 24 is illustrated in a filled or dilated state due to being "filled" with the fluid previously retained within the first fluid containing compartment 22 prior to the initiation sequence. The fluid passing between the compartments may be locked into the reservoir 24 by removing magnet 62 at any time in the urination cycle, which allows for complete emptying of the bladder of urine effortlessly by the user. The urine flows through the pathway illustrated by arrows 65 into the lumen 18 of the elongate member 12 of flow control apparatus 10, and subsequently exits the body.

Closure of the flow control apparatus 10 is accomplished by re-introduction of magnet 62 as previously explained. When magnet 62 is held at an effective location for a short time, the shape memory of the deformable dome 30 draws fluid in a direction reverse of flow arrows 64, and a sealable contact is re-established between the deformable dome 30 and sealing ring 38. Magnet 62 is then removed until the next urination event is sensed.

Figure 4:
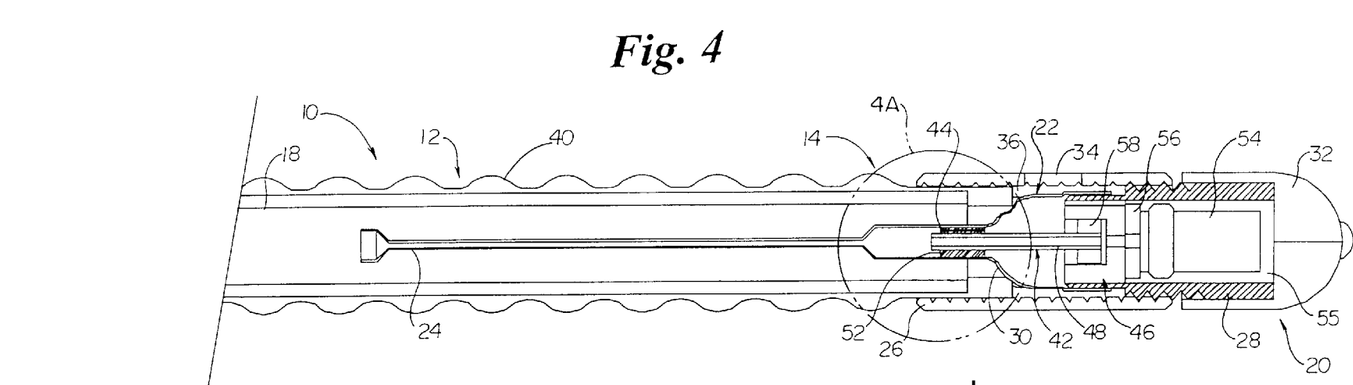
FIG. 4 is an partial longitudinal sectional view of the flow control device of the subject invention illustrating the elements of the device, and their relationships, at the onset of a dynamic condition, more particularly, an override condition.
Figure 4A:
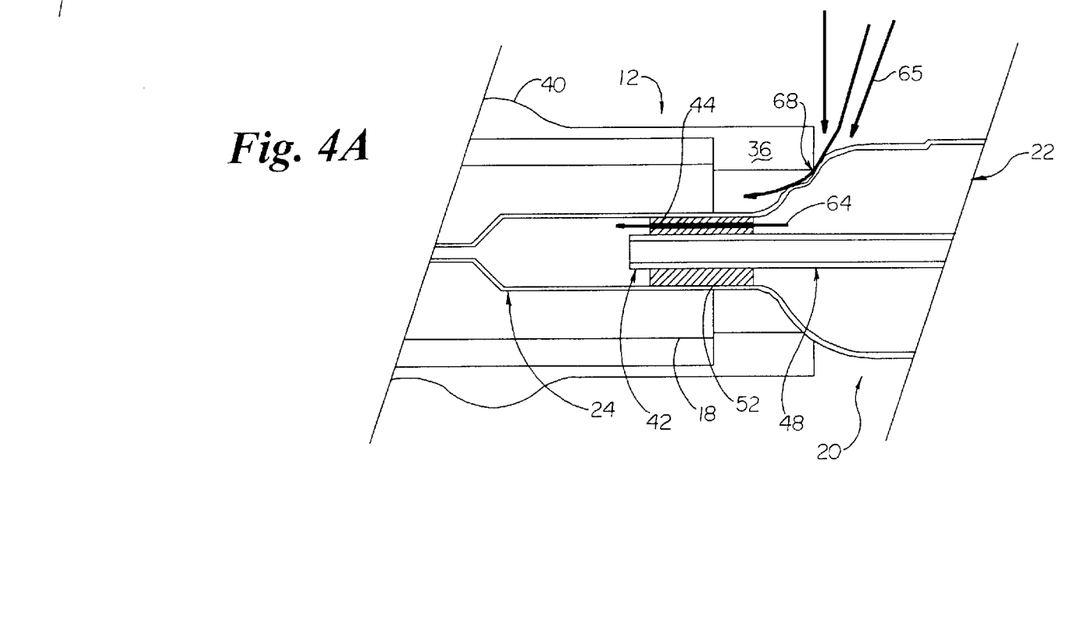
FIG. 4A is an enlarged view of the device of FIG. 4 showing urine influx from the bladder and the associated fluid element response, namely fluid displacement within the fluid element via the secondary passage.

Referring now to FIGS. 4 and 4A wherein the safety feature of over-pressure protection is illustrated, magnet 54 is sealably stable (i.e., latched) against the sealing surface 56 and conduit body 46. Fluid is thereby restricted from being moved from the first fluid containing compartment 22 through the primary fluid pathway 42, illustrated by the arrows 64 of FIG. 3) into adjacent reservoir 24. The only passage of fluid into reservoir 24 that can occur is through the secondary fluid passage 44 as illustrated by arrow 64. In this condition, the internal fluid system (i.e., the fluid containing compartments 22, 24) would normally be hydraulically locked, except for the over-pressure protection circuit which is incorporated into this device. When the pressure of the impinging urine exceeds the design specific pressure required to displace the deformable dome 30 (i.e., preferably in the range of about 25 to 40 cm $H_2O$) from contact with the sealing ring 38, the fluid is forced through the secondary fluid passage 44 into the reservoir 24. Instantaneously in response thereto, the deformable dome 30 marginally collapses so as to yield a small separation 68 between the deformable dome 30 and sealing ring 38. A small flow rate of urine will then enter the lumen 18 and into the urethra.

Secondary fluid passage 44 is dimensionally sized so that the release of urine into the lumen 18 will not occur until pressure within the bladder exceeds approximately 30 cm $H_2O$ for a time longer than approximately 2 to 6 minutes. This rate of passage of fluid into reservoir 24 is viewed by clinicians to be safely within the parameters necessary to allow for protection of the renal tract.

It is known that during events of coughing, laughter, or moderate muscular straining, urine pressure can easily exceed 20–30 cm $H_2O$, with pressures reaching as high as 150 cm $H_2O$ for short durations (i.e., usually less than 1 second per event). When these events occur, fluid will pass through the secondary fluid passage 44 into the reservoir 24. Even though the momentary pressures within the bladder are very high, the device 10 will not initiate a leak unless there are very rapid sequential events. The rate of passage of fluid into reservoir 24 is determined by the internal geometry of the secondary fluid passage 44. The internal geometry is selected to provide a balance between the pressure event duration and rate of passage opening, such that the device in effect may distinguish between the character of the over pressurization event, namely a discrete event such as coughing or straining on the one hand, and a more critical "unhealthy" chronic pressure increase or build up.

In the preferred embodiment, the secondary fluid passage is approximately 0.004 inches in diameter, hydraulic diameter equivalent, and in excess of about 0.075 inches in length. Passage 44 is preferably constructed by forming the silicone material with which conduit body 46 is constructed so as to produce such passage, as for instance by placement of a mandrel within the curing silicone, and removing same upon full cure, thereby leaving fluid passage 44 in tact.

The fluid of the fluid element preferably has a viscosity of approximately 100 centipoise. It would be obvious to those skilled in fluid mechanics that changes in flow control assembly dimensions particulars (e.g., geometry, dimensions, materials of construction) directly effect the character (i.e., physical properties) of the fluid, and that numerous combinations can produce similarly desirable time delays for handling discrete bladder pressure impulses that typically are minimal.

It should be appreciated that the functional feature of high pressure activation may be eliminated by omission of the secondary passage 44. This may be beneficial for certain user populations such as those who have excessive frequency of straining events. It may be further appreciated that by the elimination of magnet 54, urethral flow control device 10 will function as a pressure actuated flow control apparatus. The conditions that determine the threshold of actuation are then regulated by the mechanical characteristics of the deformable dome 30, and the interior dimensions of conduit 48, or alternatively the secondary fluid passage 44. Such alterations of the device of the subject invention are contemplated for the treatment of urinary incontinence.

Figure 5:
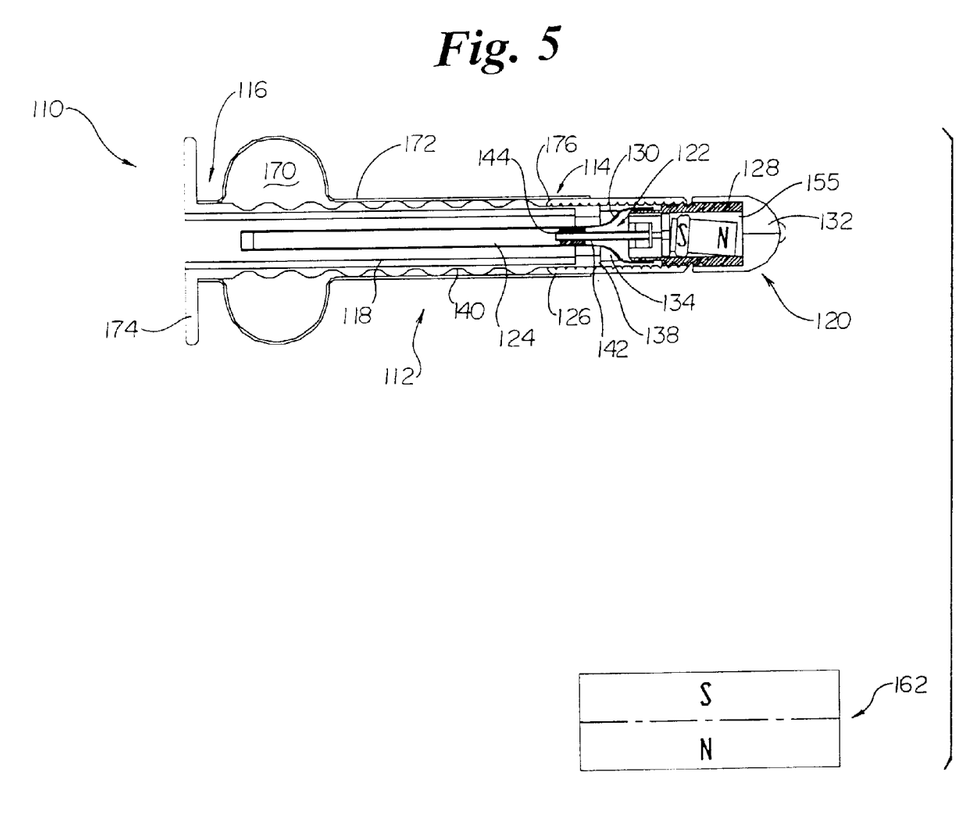
FIG. 5 is a longitudinal sectional view of an alternate embodiment of the subject invention, shown in a dynamic condition.
Figure 5A:
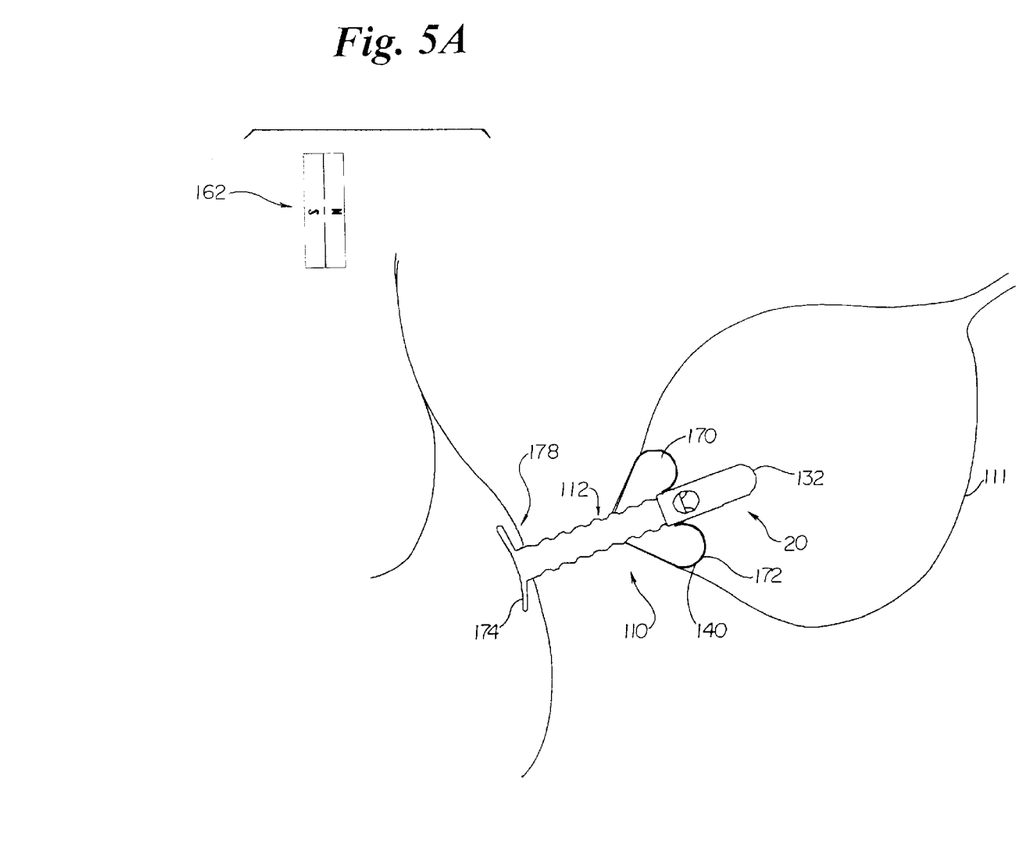
FIG. 5A is a schematic view of the device of FIG. 5 shown in situ, namely in a female urinary system.

Referring now to FIGS. 5 and 5A, there is illustrated an alternate embodiment of the urinary flow control device of the subject invention, one especially adapted to be placed in a human female. The device 110 generally includes an elongate member 112 having proximal 114 and distal 116 ends in a lumen 118 capable of discharging there through, and a flow control assembly 120, operatively joined to the elongate member 112, having first 122 and second 124 fluid containing compartments adapted to be in fluid communication with each other. Elongate member 112 and flow control assembly 120 are operatively and structurally similar to the device heretofore discussed. A fluid "bulb" 170 is co-axially encompassing elongate member 112 for "travel" (i.e., variable positioning) with respect thereto. Bulb 170 is formed along the length of elongate member 112 by the anatomically responsive distribution of a physiologically inert fluid captured or sealed between an exterior surface 140 of elongate member 112 and a fluid containing layer 172 thereover. Bulb 170 terminates at the distal extremity of the elongate member 112 at a meatal pad 174. Bulb 170 terminates at the proximal extremity at a bulb-casing termination 176 (i.e., the interface of layer 172 with casing 126).

When device 110 is inserted for use, the meatal pad 174 is generally in contact with the meatus 178 of the urethra, with bulb 170 positioned within the bladder. As shown in FIG. 5, bulb 170 is in a first static state (i.e., a pre-deployment condition), with the fluid oriented near the distal extremity of the device 110. FIG. 5A illustrates bulb 170 being formed so as to be within the bladder, more particularly near the bladder neck, this orientation being a second stable state, namely, an anchoring configuration. The fluid will remain in this position until the urethral flow control device 110 is slowly and gently withdrawn. The pressure of the urethra and the underlying sphincter will restrain the fluid from returning to the distal extremity under normal conditions thus restricting the urethral flow control device 110 from being expelled. When pressure on urine impinges upon urethral flow apparatus 110, slight movement in the distal direction may occur. If this does, bulb 170 interferes with the movement by increasing the contact pressure against the bladder neck (i.e., reacts in a wedge-like manner). Meatal pad 174 provides for a comfortable limiter to prohibit movement of urethral flow control device 110 toward the bladder by spanning the meatus 178.

For females that are inconvenienced with urinary incontinence due to sphincter insufficiency, the need for pressure override protection may be obviated due to the ease of device removal. This override protection function would be preferably utilized for males and all institutionalized or geriatric patents or spinal cord injury patents due to the lack of reliable physiological or sensory feedback.

Figures 6, 7:
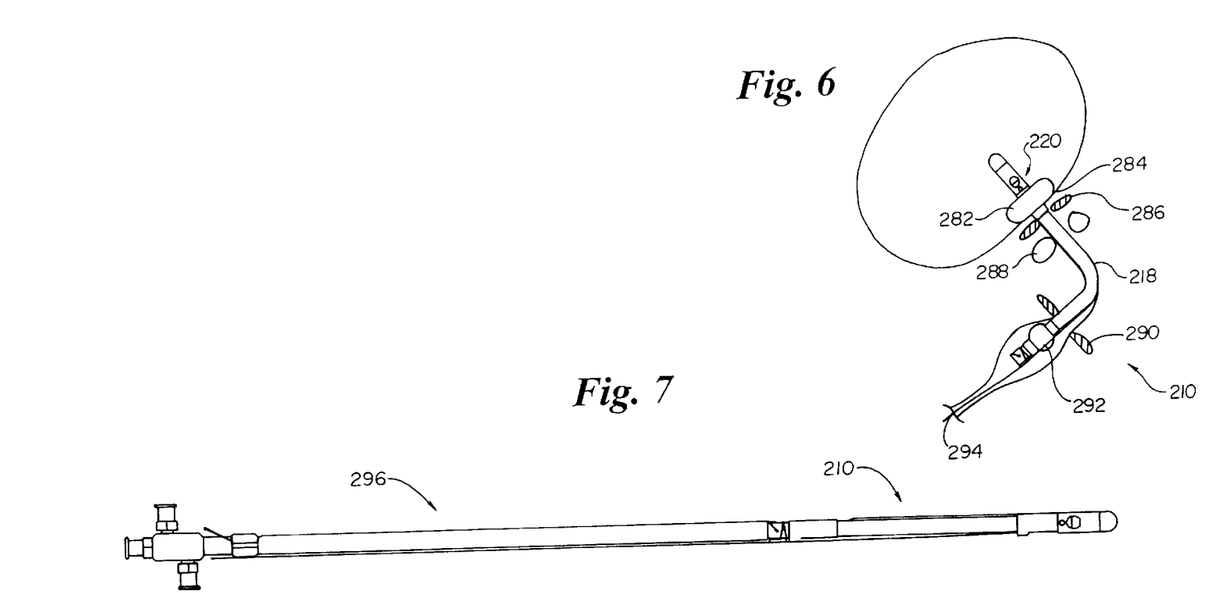
FIG. 6 is a schematic view of a further embodiment of the flow control device of the subject invention shown in situ, namely in a male urinary system.
FIG. 7 is a schematic view of a device delivery apparatus, showing the device of FIG. 6 in a predeployment condition; and, FIG. 7A is a view similar to that of FIG. 7 but instead showing the anchoring mechanism in an activated state.

Referring now to FIG. 6, urinary flow control device 210 is illustrated indwelling in the male urethra. This device operates to release urine in the identical manner as the prior embodiments. Sought after flow control functions are provided by flow control assembly 220 which is mounted on the proximal extremity of the device body. This embodiment provides for an alternative positioning and anchoring mechanism. Adjacent the flow control assembly 220, proximal balloon 282 is in a filled condition, resting adjacent bladder base 284 near internal sphincter 286. The device body extends through the interior of bladder base 284, through the urethra in the regions of the internal sphincter 286, prostate 288, external sphincter 290, and terminates within interior of the bulbous urethra. A distal balloon 292 is located at the distal extremity of device body such that, in use, distal balloon 292 dwells in the bulbous urethra (i.e., occupies a portion thereof to aid device positioning and retention). The function of proximal balloon 282, and distal balloon 292 are to restrict the flow control apparatus 210 from moving either towards the bladder, or distally into the urethra. Tether 294 provides for ease of removal of flow control apparatus 210.

Figure 7A:
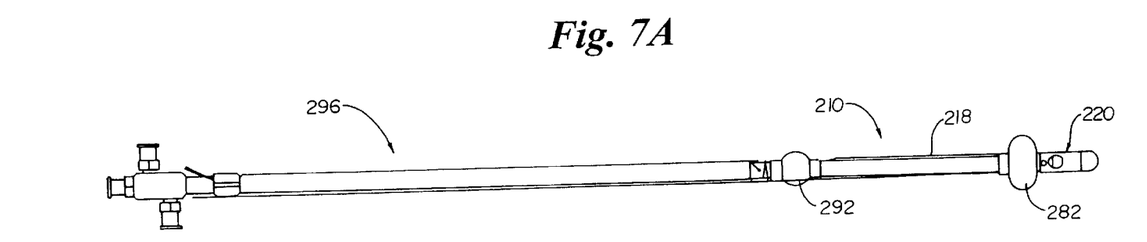

Referring now to FIGS. 7 and 7A, flow control apparatus 210 is illustrated on an insertion device 296. FIG. 7 illustrates flow control apparatus 210 without fluid in balloons 282 and 292. Insertion device 296 enables the insertion and securing of device 210 into the urethra and bladder without visualization as may be provided by x-ray, cystoscopy or ultrasound. The features and method of insertion and removal of urethral device 210 are in part the subject matter of co-pending U.S. patent application No. 60/223,345, "LOWER URINARY TRACT FLOW CONTROL APPARATUS AND METHOD OF USE THEREOF"; Ser. No. 60/259,809, "LOWER URINARY TRACT FLOW CONTROL APPARATUS AND METHOD OF USE THEREOF," filed Jan. 5, 2001; and, Ser. No. 09/724,239 "Magnetic Retrieval Device & Method of Use," each of which is incorporated herein by reference.

Medical grade silicone to date is the preferred urine contact material for urological products, which are indwelling within the urethra, bladder or meatal regions due to the relative inertness of this material in cooperation with urinary tract infections. All of the contact surfaces are medical grade silicone.

One of the unique features of all the embodiments of this invention that the sealing methodology involves a silicone deformable dome which, due to the repeated change in shape at every voiding, is only minimally susceptible to interruption of service due to encrustation. The silicone sealing ring is also soft and compliant.

It may be appreciated to those familiar with the field of clinical urology that the bladder and urethra are extremely chemically hostile environments. For this reason, the flow control assembly, more particularly the fluid containing compartments, is configured to prohibit urine entry. The magnetic switch is hermetically sealed from contact with urine. The minimal pressures available for actuation of the device further requires that the fluid is mostly void of air in order for the devices to provide sufficient flow rates (>9 cc/second). The devices which have been used clinically to date have been provided with a slight internal vacuum of approximately 5 cm $H_2O$. The fluid utilized is selected according to the viscosity and biocompatibility. The current fluid utilized is a low viscosity silicone fluid. Alternative fluids may be utilized such as olive oil, or other fluids which meet the viscosity requirements and which are preferably hydrophobic and relatively inert to the silicone or other material of the deformable dome and surrounding components.

Similar materials such as medical grade silicones enhanced with anti-microbial elements such as polyethylene glycol, silver, silver ions, or alloys may be utilized to alter the physiological interaction with the urinary tract and urine. Other antibiotics may further be compounded within the silicone or other elastomers to provide similar mechanical functions while delaying the onset of device corrosion or encrustation. It would be apparent to those skilled in the art that the configurations and parameters may be varied slightly to accomplish similar functions without deviating from the scope and intent of this invention.

This invention disclosure provides device configurations which achieve this function and method. There are other variations of this invention which will become obvious to those skilled in the art. It will be understood that this disclosure, in many respects, is only illustrative. Changes may be made in details, particularly in matters of shape, size, material, and arrangement of parts without exceeding the scope of the invention. Accordingly, the scope of the invention is as defined in the language of the appended claim.

What is claimed is:

1. A urinary flow control device comprising:
   a. an elongate member having proximal and distal ends, and a lumen capable of discharging urine therethrough; and,
   b. a sealed flow control assembly comprising first and second fluid containing compartments adapted to be in fluid communication, said sealed flow control assembly operatively joined to said elongate member such that urine entering said elongate member impinges upon said first fluid containing compartment, said flow control assembly being responsive to increased bladder pressure such that fluid is displaced from said first fluid containing compartment to said second fluid containing compartment to thereby permit select passage of the urine entering said elongate member to said lumen thereof for discharge therethrough.

2. The device of claim 1 wherein a primary fluid passage connects said first fluid containing compartment with said second fluid containing compartment, said primary fluid passage capable of selective passage of fluid between said fluid compartments in furtherance of passage of urine from the bladder to said lumen.

3. The device of claim 2 wherein said flow control assembly further includes a latch disposed to prohibit the flow of fluid from said first fluid containing compartment to said primary fluid passage.

4. The device of claim 3 wherein said latch is capable of remote manipulation to permit displacement of fluid from said first fluid containing compartment to said second fluid containing compartment.

5. The device of claim 4 wherein said latch is magnetically activated.

6. The device of claim 5 wherein unlatching of said latch is initiated by means external to said device.

7. A urinary flow control device comprising:
   a. an elongate member having proximal and distal ends, and a lumen capable of discharging urine therethrough; and,
   b. a flow control assembly comprising first and second fluid containing compartments joined by primary and secondary fluid passages, said flow control assembly operatively joined to said elongate member and adapted to receive and contain urine from a bladder so as to impinge upon said first fluid containing compartment, said flow control assembly being responsive to increased bladder pressure such that fluid is displaced from said first fluid containing compartment to said second fluid containing compartment via said primary fluid passage to thereby permit select passage of received urine to said lumen for discharge therethrough, said a secondary fluid passage permitting fluid communication between said first fluid containing compartment with said second fluid containing compartment so as to provide automatic pressure relief to the bladder by displacement of fluid from said first fluid containing compartment to said second fluid containing compartment.

8. The device of claim 7 wherein fluid is displaced from said first fluid containing compartment to said second fluid containing compartment via said secondary fluid passage during discrete pressure impulse events transmitted by the bladder in furtherance of bladder pressure relief.

9. The device of claim 8 wherein a bladder pressure impulse of about 10 to 100 centimeters of water motivates passage of fluid from said first fluid containing compartment to said second fluid containing compartment.

10. The device of claim 8 wherein a bladder pressure impulse of about 20 to 50 centimeters of water motivates passage of fluid from said first fluid containing compartment to said second fluid containing compartment.

11. The device of claim 1 wherein said sealed flow control assembly has a static configuration and a dynamic configuration, said static configuration blocking the passage of urine from the bladder to said lumen, said dynamic configuration permitting drainage of urine from the bladder to said lumen.

12. The device of claim 11 wherein said static configuration comprises said first fluid containing compartment completely abutting an interior portion of said sealed fluid control assembly so as to form a fluid seal capable of blocking the passage of urine to said lumen.

13. The device of claim 12 wherein said dynamic configuration comprises said first fluid containing compartment partially abutting said interior portion of said fluid control assembly so as to prevent the formation of said fluid seal, thereby permitting passage of urine to said lumen in furtherance of bladder relief.

14. The device of claim 1 wherein said first fluid containing compartment comprises an element having an elastic character.

15. The device of claim 14 wherein said element is configured to be semihemispherical.

16. The device of claim 14 wherein said element has a dome-like configuration.

17. The device of claim 14 wherein said second fluid containing compartment is expansible.

18. An indwelling urinary flow controller comprising:
a. a controller body for engaging a portion of a bladder, said controller body adapted to receive urine from the bladder;
b. a fluid reservoir; and,
c. a fluid containing capsule adapted to be in fluid communication with said fluid reservoir so as to define a sealed fluid assembly, said fluid containing capsule having a deformable membrane responsive to urine received by said controller body such that fluid passes between said fluid containing capsule and said reservoir with changes in bladder pressure, said sealed fluid assembly positioned within said controller body such that said deformable membrane sealingly engages an interior portion thereof to block discharge of urine received by said controller body from said flow controller, said deformable membrane being responsive to increased bladder pressure such that fluid passes from said fluid capsule to said fluid reservoir so as to disengage at least a portion of said deformable membrane from said interior portion of said controller body to permit drainage of urine from said controller body.

19. In a urethral catheter adapted to receive urine from a bladder, a flow control device for regulating egress of urine from the bladder, said device subject to bladder pressure and comprising a sealed fluid element having a first fluid region, a second fluid region, and a hydraulic linkage therebetween, said sealed fluid element being hydraulically responsive to a range of preselected bladder pressure such that fluid within said sealed fluid element shuttles from one of said fluid regions to another of said fluid regions, thereby permitting selective urine discharge via the urethral catheter.

20. The device of claim 21 wherein a portion of one of said fluid regions traverses a lumen of the urethral catheter, thereby blocking discharge of urine via the urethral catheter.

21. The device of claim 19 wherein a portion of one of said fluid regions traverses a lumen of the urethral catheter so as to thereby form a fluid seal capable of blocking the discharge of urine via the urethral catheter.

22. The device of claim 21 wherein the lumen traversing portion of one of said fluid regions is physically responsive to varying bladder pressure.

23. The device of claim 21 wherein said fluid seal is physically responsive to varying bladder pressure.

24. The device of claim 21 wherein the lumen traversing portion of one of said fluid regions comprises a reversibly deformable wall.

25. The device of claim 21 wherein the lumen traversing portion of one of said fluid regions comprises an elastomeric member.

26. The device of claim 25 wherein said elastomeric member comprises a semihemispherical element.

27. The device of claim 21 wherein said hydraulic linkage is selectively operable in furtherance of actively shuttling fluid between said fluid regions of said sealed fluid element.

28. The device of claim 27 wherein said sealed fluid element includes over pressure protection means for emergent egress of urine from the bladder.

29. The device of claim 28 wherein said emergent egress of urine from the bladder is initiated by a physiological response of said means to bladder pressures in excess of about 20 cm of water.

30. The device of claim 29 wherein said means comprises a passage between said first and second fluid regions of said sealed fluid element.

31. The device of claim 30 wherein said passage is unregulated.

32. The device of claim 30 wherein said hydraulic linkage includes a valve.

33. The device of claim 32 wherein said valve is remotely operable.

34. The device of claim 33 wherein said hydraulic linkage includes a latch.

35. The device of claim 34 wherein said latch is magnetically activated.

36. The device of claim 35 wherein unlatching of said latch is initiated by means external to said device.

* * * * *